United States Patent [19]
Haga et al.

[11] Patent Number: 5,168,113
[45] Date of Patent: Dec. 1, 1992

[54] MERCAPTO-SUBSTITUTED PYRIDINE COMPOUNDS

[76] Inventors: Takahiro Haga; Yasuhiro Tsujii, both c/o Ishihara Sangyo Kabushiki Kaisha Chuo Kenkyusho, 3-1, Nishishibukawa 2-chome, Kusatsu-shi, Shiga-ken; Tatsuo Isogai, c/o Ishihara Sangyo Kabushiki Kaisha Yokkaichi Plant, 1, Ishihara-cho, Yokkaichi-shi, Mie-ken; Shigeo Murai, c/o Ishihara Sangyo Kabushiki Kaisha Chuo Kenkyusho, 3-1, -Nishishibukawa 2-chome, Kusatsu-shi, Shiga-ken; Hisayoshi Jonishi, c/o Ishihara Sangyo Kabushiki Kaisha Chuo Kenkyusho, 3-1, Nishishibukawa 2-chome, Kusatsu-shi, Shiga-ken; Tokiya Kimura, c/o Ishihara Sangyo Kabushiki Kaisha Chuo Kenkyusho, 3-1, Nishishibukawa 2-chome, Kusatsu-shi, Shiga-ken; Hiroshi Sasaki, c/o Ishihara Sangyo Kabushiki Kaisha Chuo Kenkyusho, 3-1, Nishishibukawa 2-chome, Kusatsu-shi, Shiga-ken; Takao Awazu, c/o Ishihara Sangyo Kabushiki Kaisha Chuo Kenkyusho, 3-1, Nishishibukawa 2-chome, Kusatsu-shi, Shiga-ken; Toshihiro Tanaka, c/o Ishihara Sangyo Kabushiki Kaisha Chuo Kenkyusho, 3-1, Nishishibukawa 2-chome, Kusatsu-shi, Shiga-ken, all of Japan

[21] Appl. No.: 471,337

[22] Filed: Jan. 29, 1990

Related U.S. Application Data

[63] Continuation-in-part of Ser. No. 217,021, Jul. 11, 1988, abandoned, and Ser. No. 389,647, Aug. 4, 1989, abandoned.

[30] Foreign Application Priority Data

| Jul. 10, 1987 | [JP] | Japan | 62-172452 |
| Feb. 24, 1988 | [JP] | Japan | 63-41269 |
| Mar. 26, 1988 | [JP] | Japan | 63-72771 |
| Aug. 4, 1988 | [JP] | Japan | 63-194812 |
| Aug. 12, 1988 | [JP] | Japan | 63-201525 |
| Aug. 23, 1988 | [JP] | Japan | 63-208770 |
| Apr. 17, 1989 | [JP] | Japan | 1-97219 |

[51] Int. Cl.$^5$ .............................. C07D 213/89
[52] U.S. Cl. ............................ 546/292; 546/290; 546/298
[58] Field of Search ............. 546/292, 290, 298

[56] References Cited

U.S. PATENT DOCUMENTS

| 3,759,932 | 9/1973 | Gavin et al. | 546/290 |
| 4,435,206 | 3/1984 | Levitt | 71/92 |
| 4,518,776 | 5/1985 | Meyer et al. | 544/206 |
| 4,521,597 | 6/1985 | Kristinsson et al. | 544/3 |
| 4,548,942 | 11/1985 | Shroot et al. | 514/301 |
| 4,786,734 | 11/1988 | Hanagan | 546/293 |

FOREIGN PATENT DOCUMENTS 232067 8/1987 European Pat. Off.
237292 9/1987 European Pat. Off.

OTHER PUBLICATIONS

Blank et al., "Mercaptopyridinecarboxylic Acids, Synthesis and Hypoglycemic Activity"; Journal of Medicinal Chemistry; vol. 17, No. 10, pp. 1065–1071; 1974.

Blank et al., "Synthesis and Hypoglycemic Activity of 4-Substituted 3-Mercaptopicolinic Acids", Journal of Medicinal Chemistry; vol. 20, No. 12, pp. 1572–1577, 1977.

Primary Examiner—Mary C. Lee
Assistant Examiner—Jacqueline Haley

[57] ABSTRACT

A mercapto-substituted pyridine compound having formula (I):

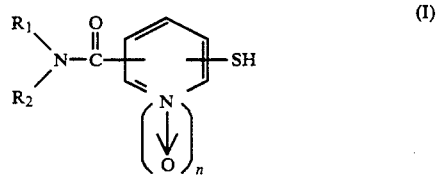

where $R_1$ and $R_2$ are alkyl groups, and n is 0 or 1, and salts thereof and a process for preparing the same are disclosed. The mercapto-substituted pyridine compound is useful as an intermediate for preparing a herbicidal compound.

The present invention further provides aminocarbonyl-substituted pyridinesulfinic acid (ACPS) or salts thereof as the precursor of aminosulfonyl-substituted pyridine-carbonic acid amide compound (APCA) which is useful as the starting material for agricultural chemicals, medicine, etc. Moreover, the preparation process of the present invention is an industrially advantageous preparation process which is capable of preparing in a series of steps from mercapto-substituted pyridinecarboxylic acid amide compound (MPCA) or aminocarbonyl-substituted halogenopyridine compound (ACHP) to ACPS or salts thereof, and further to APCA.

4 Claims, No Drawings

MERCAPTO-SUBSTITUTED PYRIDINE COMPOUNDS

This application is a continuation-in-part application of U.S. application Ser. No. 07/217,021, filed July 11, 1988, now abandoned, and U.S. application Ser. No. 07/389,647, filed Aug. 4, 1989, now abandoned.

FIELD OF THE INVENTION

The present invention relates to novel mercapto-substituted pyridine compound and salts thereof, and to a process for preparing the same.

The present invention also relates to novel aminocarbonyl-substituted pyridinesulfinic acid (hereinafter referred to as ACPS), or salts thereof as a precursor of an aminosulfonyl-substituted pyridinecarboxylic acid amide compound (hereinafter referred to as APCA) useful as the starting material of agricultural chemicals, medicines, and the like, and to an industrially advantageous process for preparing the same.

BACKGROUND OF THE INVENTION

The mercapto-substituted pyridine compound of the present invention is characterized by having an aminocarbonyl group on the pyridine ring, said aminocarbonyl group being substituted by two alkyl groups. Certain substituted pyridine compounds are disclosed in the respective specifications of U.S. Pat. Nos. 3,759,932; 4,435,206, 4,518,776 and 4,521,597. However, the above specifications fail to disclose the aforementioned mercapto-substituted pyridine compound on the pyridine ring. Also U.S. Pat. No. 4,548,942 discloses 2-mercaptonicotinamides represented by formula (4) in column 7. These compounds are useful for preparing derivatives of (5,4b)-isothiazolo pyridine-3-one as an anti-acne agent. The patented compounds do not chemically overlap with those of the present invention, the aminocarbonyl group being substituted by only one alkyl group, and the disclosed utility is quite different from the present invention.

European Patent Application Laid-Open Nos. 237,292 and 232,067 disclose a process for preparing APCA. However, the process disclosed therein is not always satisfactory industrially because of low yield, increased reaction steps, necessity of isolation in respective reaction steps, or of using reactants which are difficult to handle and expensive.

The present inventors made various studies in order to find an industrially advantageous process for preparing APCA and, as a result, found out that a process by way of ACPS or salts thereof according to the present invention is capable of providing the intended effects to complete the present invention.

SUMMARY OF THE INVENTION

The present invention provides a mercapto-substituted pyridine compound having the general formula (I):

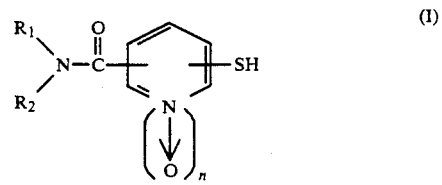

where $R_1$ and $R_2$ are alkyl groups, and n is 0 or 1, and salts thereof.

The alkyl groups in $R_1$ and $R_2$ of the general formula (I) include those having 1 to 6 carbon atoms, for example, methyl group, ethyl group, propyl group, butyl group and the like.

The salt of the mercapto-substituted pyridine compound includes acid addition salts, alkali metal salts and the like, and specifically includes salts of the mercapto-substituted pyridine compounds of the general formula (I) where n is 0, with an alkali metal such as lithium, sodium, potassium or the like.

Among the mercapto-substituted pyridine compounds and salts thereof, the compounds having the general formula (I'):

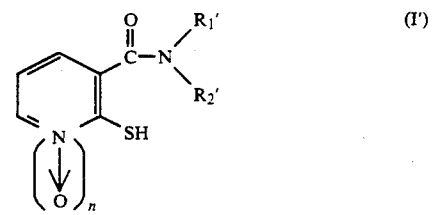

where $R_1'$ and $R_2'$ are alkyl groups and n is as defined above, and salts thereof are preferred, and further such a combination that $R_1'$ is a methyl group and $R_2'$ is a methyl group in the general formula (I'), is more preferred.

The present invention also provides an aminocarbonyl-substituted pyridinesulfinic acid having the general formula (V):

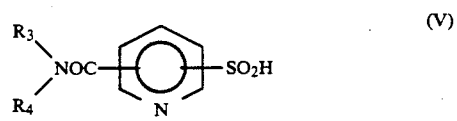

where $R_3$ and $R_4$ are hydrogen atoms or alkyl groups as defined above, respectively, or salts thereof. Examples of the salts of formula (V) include salts of alkali metal or alkaline earth metal such as lithium, sodium, potassium, magnesium, calcium and the like; amine salts due to amines substituted with hydrocarbon group such as triethylamine, dimethylamine and the like; quaternary ammonium salts such as ammonium salt due to ammonia and the like; and the like.

Of the above ACPS or salts thereof, a compound having the general formula (V"):

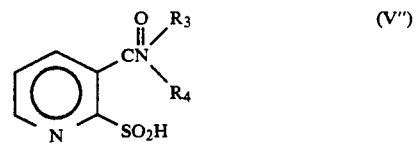

where $R_3$ and $R_4$ are as defined above, or salts thereof are preferred, and such a combination that $R_3$ is hydrogen atom or methyl group and $R_4$ is methyl group in the general formula (V''), is more preferred. Of the above ACPS or salts thereof, the salts are preferred. Of the salts, alkali metal salts and ammonium salts are preferred, and sodium is more preferred.

The mercapto-substituted pyridine compound of the present invention may be prepared, as shown by the following equation:

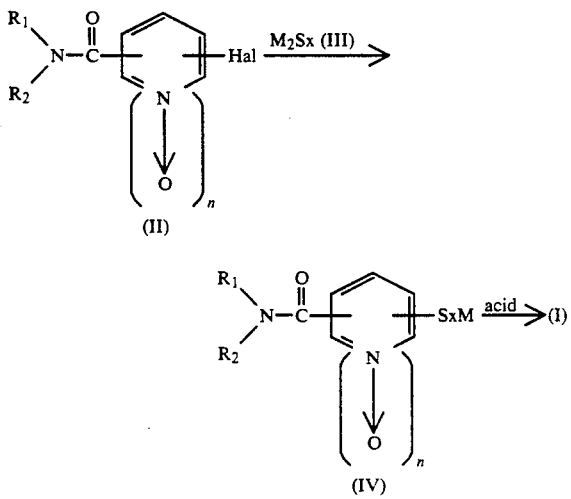

where M is alkali metal, x is 2 to 8, Hal is halogen atom, and $R_1$, $R_2$ and n are as defined above, by a synthetic reaction of pyridinepolysulfide in which a halogeno-substituted pyridine compound having the general formula (II) is reacted with a polysulfide having the general formula (III) followed by an acid treatment.

The above ACPS or salts thereof according to the present invention may be prepared by the following process:

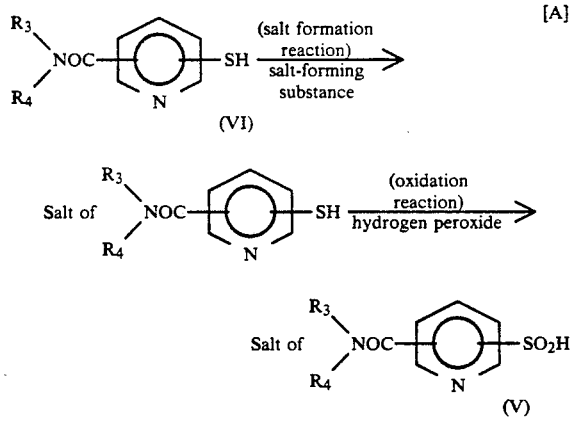

where $R_3$ and $R_4$ are as defined above.

DETAILED DESCRIPTION OF THE INVENTION

A. Mercapto-Substituted Pyridine Compounds

1. Preparation of the Halogen-Substituted Pyridine Compound

The halogeno-substituted pyridine compound may be easily prepared, for example, by reacting thionyl chloride with a halogenopicolinic acid or halogenonicotinic acid or halogenoisonicotinic acid followed by reacting with amines in a solvent such as methylene chloride. Among the halogeno-substituted pyridine compounds, such ones that the halogen atom located at 2, 4 or 6 position of the pyridine ring are desirable, and the halogen atom therein is desirably chlorine atom or bromine atom.

Among the compounds of the general formula (II), N-oxide compounds may usually be prepared by dissolving the halogeno-substituted pyridine compound in a solvent such as water, alcohols, ethers, esters, nitriles, aliphatic hydrocarbons unsubstituted or substituted by halogen atom, fatty acids unsubstituted or substituted by halogen atom and aromatic hydrocarbons, preferably water and fatty acid unsubstituted or substituted by halogen atom to be reacted with a peroxide. The amount of the solvent used is normally 10 to 10,000% by weight based on the halogeno-substituted pyridine compound. The peroxide includes organic peracids such as perbenzoic acid, metachloroperbenzoic acid, monoperoxyphthalic acid, performic acid, peracetic acid or trifluoroperacetic acid, organic peracid esters such as tert-butyl peracetate or tert-butyl perbenzoate, alkylhydroperoxides such as tert-butyl-hydroperoxide or tert-amylhydroperoxide, or hydrogen peroxide, preferably performic acid, peracetic acid, trifluoroperacetic acid or hydrogen peroxide. The amount of the peroxide used is 1 to 10 moles, preferably 2 to 5 moles per one mole of the halogeno-substituted pyridine compound. The reaction temperature is normally 0° to 120° C., preferably 30° to 100° C., and the reaction time is generally 1 to 10 hours.

2. Synthetic Reaction of Pyridinepolysulfide

The polysulfide used may include those obtained beforehand by reacting 1 to 7 moles, desirably 1 to 2 moles of sulfur with one mole of a mixture of an alkali metal hydroxide and a hydrosulfide thereof, or with one mole of an alkali metal sulfide according to the conventional process, and may also include those formed in the reaction system by reacting the above reactants in the presence of the halogeno-substituted pyridine compound of the general formula (II) to be directly used in situ. The alkali metal used in the alkali metal hydroxide, the hydrosulfide thereof or the sulfide thereof may include lithium, sodium and potassium, preferably sodium. The amount to be used of the hydroxide, hydrosulfide or sulfide is 0.75 to 5 moles, desirably 1 to 1.5 moles, respectively, per one mole of the halogeno-substituted pyridine compound. Normally water may be used as a solvent in the above reaction, but an organic solvent miscible with polysulfide and water may also be used. Examples of the organic solvent may include lower alcohol such as methanol, ethanol and propanol, polyalcohol such as ethylene glycol or propylene glycol, ethers such as tetrahydrofuran, an aprotic polar solvent such as dioxane or dimethylsulfoxide, ketones such as methyl ethyl ketone, nitriles such as acetonitrile, and the like. The amount of the solvent used is normally 10 to 1000% by weight, desirably 10 to 100% by weight based on the halogeno-substituted pyridine compound. Other reaction conditions of the above reaction may not be generally defined, but the reaction temperature is normally 0° C. to reflux temperature, desirably 80° to 150° C., the reaction pressure is atmospheric pressure to several atoms, and the reaction time is generally 0.5 to 30 hours.

3. Acid Treatment

Since according to the above reaction, the mercapto-substituted pyridine compound is usually formed as an alkali metal salt of polysulfide, application of the conventional acid treatment to the reaction product results in liberating the intended mercapto-substituted pyridine compound, generating hydrogen sulfide gas, and in forming sulfur. The acid treatment is carried out, for example, by adding a non-oxidative mineral acid such as a concentrated hydrochloric acid or a dilute sulfuric acid to the reaction product in such an amount that the pH therein becomes 3 or lower, followed by subjecting to the conventional purification and separation procedure, resulting in making it possible to isolate the intended mercapto-substituted pyridine compound.

Typical examples of the mercapto-substituted pyridine compound having the general formula (I) and salts thereof are shown as follows:

| | |
|---|---|
| Compound No. 1: | N,N-dimethyl-2-mercaptonicotin-amide, m.p. 214-215° C. |
| Compound No. 2: | sodium salt of N,N-dimethyl-2-mercapto-nicotinamide. m.p. 267-271° C. |
| Compound No. 3: | N,N-dimethyl-2-mercaptonicotin-amide-1-oxide, m.p. 115.5-118° C. |
| Compound No. 4: | N,N-diethyl-2-mercapto-nicotinamide, m.p. 207-210° C. |
| Compound No. 5: | sodium salt of N,N-diethyl-2-mercapto-nicotinamide |
| Compound No. 6: | N,N-diethyl-2-mercaptonicotin-amide-1-oxide |
| Compound No. 7: | 4-(N,N-dimethylaminocarbonyl)-2-mercapto-pyridine |

Application of the above mercapto-substituted pyridine compound and salts thereof to oxidation and halogenation reaction results in obtaining halogenosulfonyl-substituted pyridine compound.

The oxidation and halogenation process may include a process in which the mercapto-substituted pyridine compound and salts thereof are reacted with a halogenating agent such as chlorine gas, bromine or the like in the presence of water, an aqueous hydrochloric acid solution, acetic acid or an aqueous acetic acid solution: a process in which the mercapto-substituted pyridine compound and salts thereof are reacted with hypochlorite or hypobromite in the presence of water or an aqueous hydrochloric acid solution, and the like, the former being desirable.

In the above processes, an aprotic organic solvent may be used to make simple the post treatment of the reaction. Examples of the solvent used include benzene, hexane, toluene, xylene, methylene chloride, chloroform, carbon tetrachloride, ethylene dichloride, trichloroethylene, diethyl ether, ethyl acetate and the like. The amount of solvent used is normally 50 to 2000% by weight based on the halogeno-substituted pyridine compound.

In the above processes, the amount of chlorine, bromine, hypochlorite, hypobromite and the like is in the range of from a theoretical amount for reaction to such an amount as to slightly exceeding the theoretical amount based on the mercapto-substituted pyridine compound and salts thereof. Similarly thereto, the amount of water, the aqueous hydrochloric acid solution, acetic acid, the aqueous acetic acid solution or the like is 50 to 2000% by weight. The aqueous hydrochloric acid solution or the aqueous acetic acid solution may be used at a concentration of 1 to 30% by weight. In the above processes, other reaction conditions are not generally defined, but the reaction temperature is normally −20° to +50° C. desirably −10° to +10° C., and the reaction time is 0.1 to 5 hours. Application of the conventional purification and separation procedures to the reaction product results in making it possible to separate halogenosulfonyl-substituted pyridine compound.

Typical examples of the halogenosulfonyl-substituted pyridine compound are shown as follows:

| | |
|---|---|
| Compound No. A: | 2-chlorosulfonyl-N,N-dimethylnicotinamide, m.p. 114-117° C. |
| Compound No. B: | 2-bromosulfonyl-N,N-dimethyl-nicotinamide, m.p. 108-111° C. |
| Compound No. C: | 2-chlorosulfonyl-N,N-diethyl-nicotinamide, oily substance |
| Compound No. D: | 2-bromosulfonyl-N,N-diethyl-nicotinamide |
| Compound No. E: | 2-chlorosulfonyl-N,N-dimethyl-nicotinamide-1-oxide. m.p. 96.5-100° C. |

Reaction of the halogenosulfonyl-substituted pyridine compound with ammonia gas or ammonia water at −10° to −100° C. leads to aminosulfonyl-substituted pyridine compound, a further reaction of which with 2-isocyanate-4,6-dimethoxypyrimidine or 2-chlorocarbonylamino-4,6-dimethoxy-pyrimidine at −10° to +100° C. easily leads to N-[(4,6-dimethoxypyrimidine-2-yl)aminocarbonyl]-3-aminocarboxyl-2-pyridine sulfonamide compound. Application of the pyridine sulfonamide compound in an amount of 0.1 to 100 g per one are makes it possible to effectively control various kinds of harmful weeds and it has such high safety for corn as to be useful as a herbicide for the corn field.

B. ACPS Compounds

The salt formation reaction and the oxidation reaction for preparation of ACPS compounds are explained in detail below.

1. Salt Formation Reaction

The salt formation reaction is normally carried out by reacting a mercapto-substituted pyridinecarboxylic acid amide compound having the general formula (V) (hereinafter referred to as MPCA) with a salt-forming substance in the presence of a solvent such as water. The amount of the solvent used is 100 to 1000% by weight relative to the weight of MPCA. Examples of the salt-forming substance include hydroxides or carbonates of alkali metal or alkaline earth metal such as lithium, sodium, potassium, magnesium, calcium and the like; amine such as triethylamine, dimethylamine or the like: ammonia such as aqueous ammonia solution, ammonia gas or the like; and the like, sodium hydroxide and ammonia being preferred. The amount of the salt-forming substance used is a reacting equivalent or more relative to MPCA, for example, 1 to 2 moles when the alkali metal salts are used, or 4 to 20 moles when ammonia is used, per one mole of MPCA respectively.

The reaction temperature may not be generally defined, but is normally 0° to 50° C., and the reaction time is generally 5 to 60 minutes.

The reaction product may be subjected to the conventional purification and separation procedures to obtain the intended salts of MPCA, or may be used for the following oxidation reaction as it is.

2. Oxidation Reaction

The oxidation reaction is carried out by dissolving or suspending the salt of MPCA in a solvent such as water followed by dropping thereinto hydrogen peroxide, or is carried out by dropping hydrogen peroxide into the reaction product obtained from the above salt formation reaction. The concentration of hydrogen peroxide is not specifically limited, but may be normally about 30% by weight, and its amount to be used is normally 1.8 to 3 moles per one mole of the salt of MPCA. The reaction temperature is not to be generally defined, but is normally 0° to 100° C., and the reaction time is generally 10 to 60 minutes.

The reaction product may be subjected to the conventional purification and separation procedures as in the case of the above salt formation reaction to isolate the salt of ACPS, neutralization of which makes it possible to obtain ACPS.

The ACPS or salts thereof, which are obtained by the above reaction, may easily be lead to APCA by amination reaction or by oxidation.condensation reaction as described below.

In an industrial practice, the salt of ACPS, which is obtained by the above reaction, may be subjected to amination reaction or to oxidation.condensation reaction as described below, in situ without being isolated. In the above case, the salt of ACPS, which is applicable to oxidation.condensation reaction, is limited to ammonium salt, when a salt other than ammonium salt of ACPS is formed, it is once converted into ammonium salt by salt conversion reaction. The salt conversion reaction is explained below.

3. Salt Conversion Reaction

The salt conversion reaction is carried out by dissolving or suspending alkali metal salts, alkaline earth metal salts or amine salts of ACPS in a solvent such as water followed by generally adding ammonia and subsequently an acid, or is carried out by generally adding ammonia and subsequently an acid to the reaction product containing the alkali metal salt, alkaline earth metal salt, or amine salt of ACPS, which has been obtained according to the above oxidation reaction. Specific examples of the ammonia used include an aqueous ammonia solution, ammonia gas and the like. The amount of the ammonia used is normally 4 to 20 moles per one mole of the alkali metal salt, alkaline earth metal salt or amine salt of ACPS. Examples of the acid include inorganic acid or organic acid such as sulfuric acid, hydrochloric acid, nitric acid, phosphoric acid, acetic acid and the like, sulfuric acid being preferred. The amount of the acid used is 1 to 4 moles per one mole of the alkali metal salt, alkaline earth metal salt or amine salt of the above ACPS. The reaction temperature is not generally defined, but is normally 0° to 50° C., and the reaction time is generally 10 to 60 minutes.

The reaction product may be subjected to the conventional purification and separation procedures to isolate ammonium salt of ACPS, but may be applicable to oxidation.concentration reaction. which is explained below, as it is in the same manner as in the case of the above reaction.

The ACPS or alkali metal salts thereof in the second embodiment of the present invention may also be prepared according to the following alternate process:

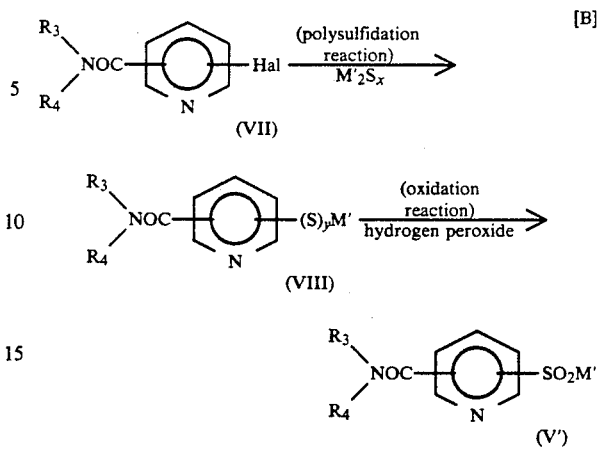

wherein $R_3$ and $R_4$ are as defined above, M' is an alkali metal element, x is 2 to 8, and y is 1 to 8.

The above polysulfidation reaction and oxidation reaction will be explained in detail.

4. Polysulfidation Reaction

On polysulfidation reaction, polysulfide used may be obtained by reacting one mole of a mixture of hydroxide and hydrosulfide of alkali metal, or of sulfide of alkali metal with 1 to 7 moles, preferably 1 to 2 moles of sulfur beforehand according to the conventional process, or may be obtained by reacting the above reactants in the presence of aminocarbonyl-substituted halogenopyridine compound (hereinafter referred to as ACHP) having the general formula (VII) to be prepared in the reaction system and to be directly used in situ. Examples of the alkali metal for the hydroxide, hydrosulfide or sulfide of alkali metal include lithium, sodium, potassium and the like, sodium being preferred. The amount of the hydroxide, hydro-sulfide or sulfide to be used is respectively 0.75 to 5 moles, preferably 1 to 1.5 moles per one mole of ACHP. In this reaction, normally water is used as a solvent, but organic solvent may also be used so long as it is miscible with polysulfide and water. Examples of the organic solvent include lower alcohol such as methanol, ethanol, propanol and the like; polyalcohol such as ethylene glycol, propylene glycol and the like; ethers such as tetrahydrofuran; an aprotic polar solvent such as dioxane, dimethylsulfoxide and the like; ketones such as methyl ethyl ketone; nitriles such as acetonitrile; and the like. The amount of the solvent used is normally 10 to 1000% by weight, preferably 10 to 100% by weight relative to the weight of ACHP. Other reaction conditions in this reaction may not generally be defined, but the reaction temperature is normally 0° C. to a reflux temperature, preferably 80° to 150° C., the reaction pressure is atmospheric pressure to several atms., and the reaction time is generally 0.t to 30 hours.

The alkali metal salt of pyridinecarboxylic acid amide (poly)sulfide having the general formula (VIII), which is obtained in the above reaction is applicable to the following oxidation reaction as it is.

5. Oxidation Reaction

The oxidation reaction may be carried out in the same manner as in the oxidation reaction of the above process [A].

The ACPS or alkali metal salts thereof, which are obtained according to this reaction, may easily be lead to APCA by an amination reaction explained below or the above salt conversion reaction—an oxidation.condensation reaction explained below.

Typical examples of ACPS or salts thereof in the present invention, which are obtained according to the above processes [A] and [B], are shown in Table 1 as follows:

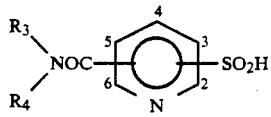

or salts thereof.

TABLE 1

| | General formula (I) or salts thereof | | | | | |
|---|---|---|---|---|---|---|
| Compound No. | Substituted position of $R_3$ $\diagdown$ NOC— $\diagup$ $R_4$ | $R_3$ | $R_4$ | Substituted position of —SO$_2$H | Kinds of salts | Physical Properites- melting point (°C.) |
| 8 | 3 | CH$_3$ | CH$_3$ | 2 | — | — |
| 9 | " | " | " | " | Na salt | 260–265 (decomposed) |
| 10 | " | " | " | " | NH$_4$ salt | 128–130 |
| 11 | " | H | " | " | Na salt | — |
| 12 | " | " | C$_3$H$_7$ (iso) | " | " | — |
| 13 | " | " | C$_2$H$_5$ | C$_2$H$_5$ | " | triethyl amine salt | — |
| 14 | " | CH$_3$ | CH$_3$ | 4 | Ca salt | — |
| 15 | " | " | " | 2 | K salt | — |

Next, the MPCA having the general formula (VI) and used as a starting material in the above process [A] may be prepared according to the following process:

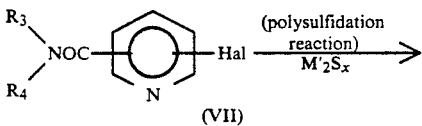

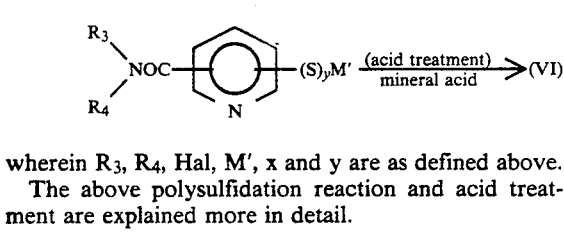

wherein $R_3$, $R_4$, Hal, M', x and y are as defined above.

The above polysulfidation reaction and acid treatment are explained more in detail.

6. Polysulfication Reaction

The polysulfication reaction may be carried out in the same manner as in the polysulfidation reaction of the above process [B].

7. Acid Treatment

The conventional acid treatment of a reaction product obtained according to the above polysulfidation reaction and containing an alkali salt of pyridinecarboxylic acid amide (poly)sulfide having the general formula (VIII) results in liberating the intended MPCA, evolving hydrogen sulfide gas, and in generating sulfur. The acid treatment is carried out by adding a mineral acid having no oxidative action, for example, concentrated hydrochloric acid, dilute sulfuric acid or the like, to the reaction product so that pH may show 3 or less, followed by conventional purification and separation procedures to isolate the intended MPCA.

Further, the ACPS or salts thereof in the present invention may be lead to aminosulfonyl-substituted pyridinecarboxylic acid amide compound (APCA) having the following general formula (IX) by the following amination reaction or oxidation.condensation reaction:

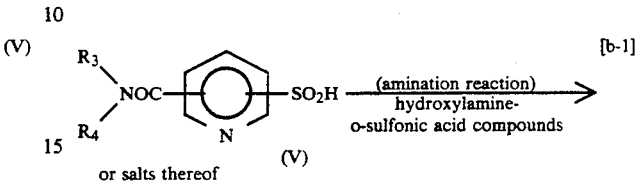

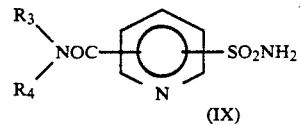

where $R_3$ and $R_4$ are as defined above.

8. Animation Reaction

The amination reaction is carried out by dissolving or suspending the above ACPS or salts thereof in a solvent such as water and adding thereto hydroxylamine-o-sulfonic acid compounds. or by adding hydroxylamine-o-sulfonic acid compounds to the reaction product obtained according to the above oxidation reaction for-reacting. Preferably, a basic substance is further added in the above reaction. The order of addition of the hydroxylamine-o-sulfonic acid compounds and of the basic substance is not specifically limited, but it is preferred to first add the hydroxylamine-o-sulfonic acid compounds and then add the basic substance. Examples of hydroxylamine-o-sulfonic acid compounds include hydroxylamine-o-sulfonic acid, o-mesitylene sulfonyl-hydroxylamine and the like, hydroxylamine-o-sulfonic acid being preferred. The amount of the hydroxyl amine-o-sulfonic acid compounds used is 1 to 3 moles per one mole of ACPS or salts thereof. Examples of the basic substance include sodium acetate, sodium carbonate, potassium carbonate, sodium hydrogencarbonate, sodium phosphate, disodium hydrogenphosphate, sodium hydroxide, potassium hydroxide, ammonia, triethylamine and the like, ammonia, sodium acetate and sodium hydroxide being preferred. The amount of the basic substance used is 0.5 to 4 reacting equivalents per one reacting equivalent of ACPS or salts thereof. The reaction temperature is not generally defined, but is normally 0° to 100° C., and the reaction time is generally 10 minutes to 24 hours.

The reaction product may be subjected to the conventional purification and separation procedures to obtain APCA.

NH₄ salt of [b-2]

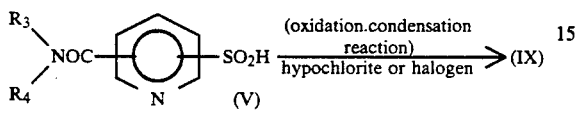

where $R_3$ and $R_4$ are as defined above.

9. Oxidation.Condensation Reaction

The oxidation.condensation reaction is carried out by dissolving or suspending ammonium salt of ACPS in a solvent such as water and adding thereto hypochlorite or halogen, or by adding hypochlorite or halogen to the reaction product obtained according to the above oxidation or salt conversion reaction and containing ammonium salt of ACPS for reacting. Examples of hypochlorite include sodium hypochlorite, potassium hypochlorite, calcium hypochlorite and the like, and examples of halogen include bromine, chlorine, iodine and the like, sodium hypochlorite being preferred. The amount to be used of the hypochlorite or halogen is 1 to 4 moles per one mole of ammonium salt of ACPS. The reaction temperature is not generally defined, but is normally −10° to +50° C., and the reaction time is generally 10 to 60 minutes.

The reaction product may be subjected to neutralization followed by the conventional purification and separation procedures to obtain APCA.

In the above process [b-2], addition of an acid makes it possible to increase yield. The acid may be added at any time during a time period from the MPCA ammonium salt formation reaction step or the reaction step of salt conversion to ammonium salt of ACPS to the oxidation.condensation reaction step, for example, between after the MPCA ammonium salt formation reaction and before the oxidation reaction, between after the oxidation reaction of ammonium salt of MPCA and before the oxidation condensation reaction, or the like. Examples of the acid include inorganic acid or organic acid such as sulfuric acid, hydrochloric acid, nitric acid, phosphoric acid, acetic acid or the like, sulfuric acid being preferred. The amount of the acid used is normally 1 to 5 moles per one mole of respective reaction products in the MPCA ammonium salt formation reaction, the salt conversion reaction to ammonium salt of ACPS, the oxidation reaction, or in the oxidation.condensation reaction.

The APCA obtained according to the above reaction may easily be lead to a substituted pyridinesulfonamide compound such as N-[(4,6-dimethoxypyrimidine-2-yl)aminocarbonyl]-3-dimethylaminocarbonyl-2-pyridine-sulfonamide and salts thereof, which are useful as herbicide for use in the corn field as disclosed, for example, in European Patent Application Laid-Open No. 232,067.

C. Examples

Examples, which are not to give any limitations to the process of the present invention, are shown below in order to describe more in detail the process of the present invention.

Examples 1-8 demonstrate processes for production of novel mercapto-substituted pyridine compounds, and Examples 9-16 demonstrate processes for production of novel aminocarbonyl-substituted pyridine sulfinic acids.

Explanations are given for compounds of the present invention as well as preparation examples of pyridine sulfonamide compound.

1. Example 1

(a) Synthetic Reaction of Pyridinepolysulfide

A mixture of 25.0 g (0.1 mole) of 96% sodium sulfide nona hydrate, 10.4 g (0.325 mole) of sulfur and 56 ml of water is refluxed by heating. At the time when sulfur dissolves completely to form a homogeneous solution, 18.45 g (0.1 mole) of 2-chloro-N,N-dimethylnicotinamide is added, followed by refluxing by heating for 18 hours to form sodium salt of N,N-dimethylnicotinamide-2-polysulfide.

(b) Acid Treatment

The above reaction product is allowed to cool down to room temperature, 15 ml of concentrated hydrochloric acid is carefully dropped (accompanying generation of hydrogen sulfide and precipitation of sulfur), and after the completion of dropping, agitation is carried out for 15 minutes. Sulfur is filtered off and washed with warm water, and the filtrate and washing liquor are confirmed to be evaporated to dryness under vacuum. The residue is repeatedly extracted with chloroform and dried over anhydrous solution sulfate, and chloroform is distilled off and the residual substance is purified with a silica gel column chromatography (developing solvent: methanol/chloroform=1/9) to obtain 17.2 g of a yellow crystalline N,N-dimethyl-2-mercaptonicotinamide (m.p. 214°-215° C.).

2. Example 2

(a) Synthetic Reaction of Pyridinepolysulfide

A mixture of 5.25 g (0.021 mole) of 96% sodium sulfide nona hydrate, 2.2 g (0.069 mole) of sulfur and 5 ml of water is refluxed by heating. At the time when the sulfur dissolves completely to form a homogeneous solution, 4.46 g (0.021 mole) of 2-chloro-N,N-diethyl-nicotinamide is added, followed by being refluxed by heating for 10 hours to form a sodium salt of N,N-diethylnicotinamide-2-polysulfide.

(b) Acid Treatment

After the above reaction product is allowed to cool down to room temperature, 4 ml of concentrated hydrochloric acid is carefully dropped (accompanying generation of hydrogen sulfide and precipitation of sulfur). After the completion of dropping procedure, agitation is further carried out for 15 minutes. The aqueous phase is extracted with dichloromethane, followed by drying and distilling off the solvent under vacuum and purification of the residue with a silica gel column chromatography (developing solvent: methanol/chloroform=1/19) to obtain 4.09 g of a yellow crystalline N,N-diethyl-2-mercaptonicotinamide (m.p. 207°-210° C.).

3. Example 3

(a) Synthetic Reaction of Pyridinepolysulfide

A mixture of 24 g (0.3 mole) of sodium hydrosulfide of 70% purity, 9.6 g (0.3 mole) of sulfur, 12 g (0.3 mole) of sodium hydroxide and 15 ml of water is refluxed by heating. At the time when the sulfur dissolves completely to form a homogeneous solution, 55.4 g (0.3 mole) of 2-chloro-N,N-dimethyl-nicotinamide is added, followed by being refluxed (125° C.) by heating for 2 hours to form a sodium salt of N,N-dimethylnicotinamide-2-polysulfide.

(b) Acid Treatment

After the above reaction product is allowed to cool down to room temperature, 150 ml of water is added and about 30 ml of concentrated hydrochloric acid is dropped so as to adjust to pH 2, while hydrogen sulfide generates and sulfur precipitates. After the completion of dropping, agitation is carried out at 60° to 70° C. for 30 minutes, followed by filtering off the sulfur while warming and by washing the residue with 150 ml of warm water to obtain filtrate and washing liquor which contain N,N-dimethyl-2-mercapto-nicotinamide.

(c) Oxidation and Bromination Reaction

The above mixture of filtrate and washing liquor is cooled with a mixture of sodium chloride and ice, 147 g (0.92 mole) of bromine is dropped with stirring at 5° C. or lower, 100 ml of a cold water is then charged to be stirred, at −5° C. for 1 hour. The reaction product is extracted with 700 ml of cold methylene chloride to obtain an extract liquor containing 2-bromosulfonyl-N,N-dimethylnicotinamide.

4. Example 4

The oxidation and bromination reaction in Example 4 is varied as follows. Into 300 ml of water is suspended 54.6 g (0.3 mole) of N,N-dimethyl-2-mercaptonicotinamide to be cooled with agitation, and 144 g (0.9 mole) of bromine is dropped at −6° C. to 0° C. After the completion of dropping above, purification procedure is carried out in the same manner as in Example 4 to obtain a methylene chloride solution containing 2-bromosulfonyl-N,N-dimethylnicotinamide. The methylene chloride solution is washed with 300 ml of ice water and 200 ml of cooled 1% aqueous solution of sodium thiosulfate, methylene chloride is distilled off at an inner temperature of 30° C. or lower, followed by drying under vacuum to obtain 76 g of reaction product. The reaction product is dissolved in warm ethylene dichloride and is recrystallized with n-hexane to obtain 64 g (yield: 72.8%) of 2-bromosulfonyl-N,N-dimethylnicotinamide (m.p. 108°–111° C.).

5. Example 5

(a) Synthetic Reaction of Pyridinepolysulfide

A mixture of 55.4 g of 2-chloro-N,N-dimethyl-nicotinamide, 24 g of sodium hydrosulfide of 70% purity, 9.6 g of sulfur, 12 g of sodium hydroxide and 15 ml of water is refluxed by heating with agitation for about 2 hours to form a sodium salt of N,N-dimethylnicotinamide-2-polysulfide.

(b) Acid Treatment

To the above reaction product are added 150 ml of water and 30 ml of a 50% aqueous sulfuric acid solution to be stirred at 60° to 70° C. for 30 minutes, and the precipitated sulfur is filtered off with warming. The sulfur is washed with 100 ml of warm water, and the filtrate and washing liquor are combined to obtain a solution containing N,N-dimethyl-2-mercaptonicotinamide.

(c) Oxidation and Bromination Reaction

The above solution is cooled down to 0° C. or lower, 350 ml of methylene chloride is added, 144 g of bromine is dropped over about 20 minutes, and a methylene chloride layer is separated to obtain a methylene chloride solution of 2-bromosulfonyl-N,N-dimethylnicotinamide.

6. Example 6

(a) N-oxidation Reaction

One hundred grams of 2-chloro-N,N-dimethylnicotinamide is dissolved in 100 ml of trifluoroacetic acid to be heated at 80° to 90° C., 240 g of 30% hydrogen peroxide water is dropped over about 1 hour, and 200 ml of trifluoroacetic acid is added to be reacted for 2 hours.

After the completion of the reaction, the water and trifluoroacetic acid in the reaction mixture are distilled off under vacuum, followed by purification with a silica gel column chromatography to obtain 56.7 g of 2-chloro-N,N-dimethylnicotinamide-1-oxide ($n^{23}{}_D{}^1$:1.5822) of 98% purity and 50.0 g of that of purity 85%.

(b) Synthetic Reaction of Pyridinepolysulfide and Acid Treatment

A mixture of 13.3 g of sodium sulfide nona hydrate, 1.6 g of sulfur and 10 ml of water is heated and dissolved to prepare sodium salt of polysulfide beforehand. Thereto is added 10 g of the 98% purity 2-chloro-N,N-dimethylnicotinamide-1-oxide-obtained in the above (a) to be reacted at 95° C. for 2 hours.

After the completion of the reaction, 30 ml of water and 10 ml of concentrated hydrochloric acid are added to the reaction mixture to precipitate sulfur, followed by filtering with warming, washing the sulfur with about 50 ml of warm water, and by combining the filtrate and washing liquor to obtain 120 ml of an aqueous solution of N,N-dimethyl-2-mercaptonicotinamide-1-oxide, a melting point of which is 115.5° to 118° C.

(c) Oxidation and Chlorination Reaction

One hundred and twenty milliliter of the aqueous solution of N,N-dimethyl-2-mercaptonicotinamide-1-oxide obtained in the above (b) is cooled to 0° to 5° C. and is subjected to reaction while introducing chlorine gas until it is not absorbed any more.

After the completion of the reaction, the reaction mixture is subjected to air buffling to remove excess chlorine, 60 ml of methylene chloride and 60 ml of water are then added for extraction, resulting in obtaining 65 ml of a methylene chloride solution of 2-chlorosulfonyl-N,N-dimethylnicotinamide-1-oxide a melting point of which is 96.5° to 100° C.

(d) Amidation

Into 65 ml of the methylene chloride solution of 2-chlorosulfonyl-N N-dimethylnicotinamide-1-oxide obtained in the above (c) is dropped 10 g of a 28% ammonia water to be reacted.

After the completion of the reaction, the reaction mixture is neutralized with concentrated hydrochloric acid, and the resulting crystallines are filtered and dried to obtain 8.0 g of 2-aminosulfonyl-N,N-dimethylnicotinamide-1-oxide (m.p.: 213°–215° C.).

7. Example 7

(a) Synthetic Reaction of Pyridinepolysulfide

A mixture of 26.4 g (0.105 mole) of 96% sodium sulfide nona hydrate, 10.8 g (0.338 mole) of sulfur and 56 ml of water is refluxed by heating. At the time when a homogeneous solution is formed, 18.45 g (0.1 mole) of 2-chloro-N,N-dimethylnicotinamide is added, followed by refluxing by heating for 20 hours to form a sodium salt of N,N-dimethyl-nicotinamide-2-polysulfide.

(b) Acid Treatment

The above reaction product is allowed to cool down to room temperature, 15 ml of concentrated hydrochloric acid is then carefully dropped. After the completion of dropping, stirring is carried out for 15 minutes to form N,N-dimethyl-2-mercaptonicotinamide.

(c) Oxidation and Chlorination Reaction

The resulting insoluble matter is filtered off and washed with warm water, the filtrate and washing liquor are combined, about 50 ml of dichloromethane is added to the combined filtrate and washing liquor to be ice-cooled, and chlorine gas is introduced thereinto. After confirming disappearance of N,N-dimethyl-2-mercaptonicotinamide, introduction of chlorine gas is stopped to form 2-chlorosulfonyl-N,N-dimethylnicotinamide (m.p. 114°–117° C.). The reaction mixture is charged into ice water, the dichloromethane layer is separated and collected, the collected dichloromethane layer is combined with one obtained by extracting the water layer with dichloromethane to be washed with water, followed by drying over anhydrous sodium sulfate and by cooling with ice water again.

(d) Amidation Reaction

Ammonia gas is introduced into the resulting dichloromethane layer at 10° C. or lower. At the time when the reaction mixture becomes weakly alkaline, introduction of ammonia gas is stopped. Dichloromethane is distilled off the reaction product, the remaining white crystals are washed with ethyl acetate followed by water, and dried to obtain 15.5 g of 2-aminosulfonyl-N,N-dimethylnicotinamide (m.p. 209°–211° C.).

(e) Condensation

A mixed solution containing 250 mg of 2-amino-4,6-dimethoxypyrimidine, 0.65 g of triethylamine and 2.5 g of ethyl acetate is dropped at 15° C. into 6.3 g of an ethyl acetate solution of 20% phosgene to be reacted for 1 hour keeping the temperature at 15° C. followed by warming in an oil bath at 90° C. to distill off excessive phosgene and ethyl acetate, adding a solution prepared by dissolving 300 mg of 2-aminosulfonyl-N,N-dimethylnicotinamide in 10 ml of acetonitrile, and by dropping 0.2 g of triethylamine to be reacted for 1 hour at room temperature.

After the completion of the reaction, the reaction product is charged into water, followed by acidifying with hydrochloric acid, filtering off deposited crystals, washing with water, and by drying to obtain 0.46 g of N-[(4,6-dimethoxypyrimidine-2-yl)aminocarbonyl]-3-dimethylaminocarbonyl-2-pyridinesulfonamide (m.p. 169°–173° C.).

8. Example 8

A field soil is packed in a 1/1.500 are pot, and seeds of various kinds of plants are sowed thereon. When respective plants reach certain plant stages in leaf number, respectively, corn: 3.2 leaf stage, wheat: 3.5 leaf stage, common cocklebur: 2.5 leaf stage, tall morning glory: 1.0 leaf stage, smartweed: 1.2 leaf stage, prickly sida: 1.0 leaf stage, slender amaranth: 0.5 leaf stage, barnyard grass: 2.0 leaf stage), a wettable powder of N-[(4,6-dimethoxypyrimidine-2-yl)aminocarbonyl]-3-dimethylaminocarbonyl-2-pyridinesulfonamide is weighed by such an amount as to be 1.25 (g/a) (as an amount of the active ingredient) to be diluted with 5L of water per one acre, followed by adding to the aqueous solution, an agricultural spreader by such an amount as to be 0.2% to be subjected to foliar application with a small-sized sprayer. Twenty four days after application, growth conditions of respective plants are observed visually and a degree of growth control is evaluated by ten grades (1: the same as in non-application area to 10: complete control). The results are shown below.

| Plants | Degree of Growth Control |
| --- | --- |
| Corn | 1 |
| Wheat | 8 |
| Common cocklebur | 10 |
| Tall morning glory | 8 |
| Prickly sida | 7 |
| Smartweed | 8 |
| Slender amaranth | 10 |
| Barnyard grass | 10 |

9. Example 9

Preparation of the starting material, MPCA (a) Polysulfidation Reaction and Acid Treatment A mixture of 55.4 g of 2-chloro-N,N-dimethylnicotinamide, 24 g of 70% purity sodium hydrosulfide, 96 g of sulfur, 12 g of sodium hydroxide and 15 ml of water is refluxed for about 2 hours by heating with agitation to form sodium salt of N,N-dimethylnicotinamide-2-polysulfide. To the above product are added 150 ml of water and 30 ml of a 50% aqueous sulfuric acid solution under stirring for 30 minutes at 60° to 70° C., and the generated sulfur is filtered off with warming. The sulfur is washed with 100 ml of warm water, and the filtrate and the washing liquor are combined together to obtain a solution containing 2-metcapto-N,N-dimethylnicotinamide. The solution is cooled down to 10° C., and deposited crystals are collected by filtration. Further, the filtrate is thickened to such an extent that the volume is reduced to about ⅓, and the deposited crystals are collected by filtration. These crystals are combined and dried to obtain 46.5 g of 2-mercapto-N,N-dimethylnicotinamide having a melting point of 200° to 208° C.

Preparation of ACPS salt of the present invention (b) Salt Formation Reaction

A 300 ml four-necked flask equipped with thermometer, dropping funnel and stirrer is charged with 18.2 g (0.1 mole) of 2-mercapto-N,N-dimethylnicotinamide, 4.4 g (0.11 mole) of sodium hydroxide and 50 ml of water to be dissolved with agitation for being reacted at room temperature for 10 minutes to obtain a reaction product containing sodium-N,N-dimethylnicotinamide-2-thiolate.

Separately, the same reaction as above is carried out to obtain a reaction product. The reaction product is thickened, and the deposited crystals are filtered off and dried to isolate 20.0 g of sodium-N,N-dimethylnicotinamide-2-thiolate having a melting point of 260° to 268° C. (a little decomposed).

(c) Oxidation Reaction

Into the reaction product obtained according to the above salt formation reaction is dropped with agitation for about 30 minutes 22.7 g (0.2 mole) of 30% aqueous hydrogen peroxide solution at a temperature of 10° to 20° C. externally cooling for reacting to obtain a reaction product containing sodium N,N-dimethylnicotinamide-2-sulfinate.

Separately, the salt formation reaction and oxidation reaction is carried out in the same manner as above to obtain a reaction product. The reaction product is thickened and dried to isolate 22.0 g of sodium N,N-dimethylnicotinamide-2-sulfinate (yield based on MPCA: 93.2%) having a melting point of 260° to 265° C. (colored brown, decomposed).

(d) Salt Conversion Reaction

To the reaction product obtained according to the above oxidation reaction as it is, is added 60.7 g (1.0 mole) of 28% ammonia water, and 12.3 g (0.125 mole) of concentrated sulfuric acid at a temperature of 10° to 20° C. is then dropped thereinto with agitation for 15 minutes for reacting to obtain a reaction product containing ammonium salt of N,N-dimethylnicotinamide-2-sulfinic acid.

Separately, the salt formation reaction, oxidation reaction and the salt conversion reaction are carried out in the same manner as above to obtain a reaction product. The reaction product is thickened and dried, and the residue is extracted with methanol and the extract liquor is dried to isolate 20.9 g of ammonium salt of N,N-dimethylnicotinamide-2-sulfinic acid (yield based on MPCA: 90.5%) having a melting point of 128° to 130° C.

Referential Example 1

Preparation of APCA: (Oxidation.Condensation Reaction)

Into the reaction product obtained according to the salt conversion reaction in Example 10, as it is, is dropped with agitation for about 30 minutes 32 g (0.2 mole) of bromine at a temperature of 10° to 20° C. for reacting, followed by stirring for 30 minutes and neutralizing with concentrated sulfuric acid to pH 3–6 to deposit white crystals. This reaction product is cooled down to about 20° C. and is then filtered, washed with water and dried to obtain 16.2 g (yield based on MPCA: 70.7%: purity: 96.5%) of 2-aminosulfonyl-N,N-dimethylnicotinamide.

10. Example 10

Preparation of ACPS salt of the present invention (a) Salt Formation Reaction

A 300 ml four-necked flask equipped with thermometer, dropping funnel and stirrer is charged with 9.1 g (0.05 mole) of 2-mercapto-N,N-dimethylnicotinamide and 45.5 of 28% ammonia water, followed by dissolving with agitation and by reacting for 10 minutes at room temperature to obtain a reaction product containing ammonium-N,N-dimethylnicotinamide-2-thiolate.

The ammonium-N,N-dimethylnicotinamide-2-thiolate (9.7 g) has a melting point of 198° to 201° C. (partly decomposed).

(b) Oxidation Reaction

Into the reaction product obtained according to the above salt formation reaction, as it is, is dropped with agitation for about 15 minutes 11.4 g (0.10 mole) of 30% aqueous hydrogen peroxide solution at a temperature of 5° to 20° C. externally cooling for reacting, followed by dropping thereinto with agitation for about 20 minutes 12.5 g (0.125 mole) of concentrated sulfuric acid at a temperature of 5° to 20° C. to obtain a reaction product containing ammonium salt of N,N-dimethylnicotinamide-2-sulfinic acid.

Separately, the ammonium salt formation reaction and oxidation reaction is carried out in the same manner as above to obtain a reaction product. The reaction product is thickened and dried, and the residue is extracted with methanol, followed by drying the extract liquor to isolate 10.8 g (yield based on MPCA: 93.5%) of ammonium salt of N,N-dimethylnicotinamide-2-sulfinic acid having a melting point of 128° to 130° C.

Referential Example 2

Preparation of APCA: (Oxidation.Condensation Reaction)

Into the reaction product obtained according to the oxidation the oxidation reaction in Example 11, as it is, is dropped with-agitation for about 30 minutes 62 g (0.1 mole) of 12% sodium hypochlorite solution at a temperature of 5° to 20° C. for reacting, followed by neutralizing with concentrated sulfuric acid to pH 3–6 to deposit white crystals. This reaction product is cooled down to about 20° C. followed by filtering, washing with water and by drying to obtain 8.5 g (yield based on MPCA: 74.2%: purity: 95.6%) of 2-aminosulfonyl-N,N-dimethylnicotinamide, 11. Example 11

Procedures of Example 11 are repeated except that dropping of 12.5 g (0.125 mole) of concentrated sulfuric acid after the completion of the oxidation reaction is replaced by dropping of 24.5 g (0.125 mole) of 50% sulfuric acid to obtain 10.5 g (yield based on MPCA: 90.9%) of ammonium salt of N,N-dimethylnicotinamide-2-sulfinic acid.

Referential Example 3

Procedures of Referential Example 2 are repeated except that the reaction product obtained according to the oxidation reaction in Example 12 is used as it is and 62 g of 12% sodium hypochlorite solution is replaced by 28 g (0.175 mole) of bromine to obtain 6.98 g (yield based on MPCA: 61.0%: purity: 98.6%) of 2-aminosulfonyl-N,N-dimethylnicotinamide.

12. Example 12

Procedures of Example 11 are repeated except that a step of dropping thereinto with agitation for about 20 minutes 12.5 g (0.125 mole) of concentrated sulfuric acid at a temperature of 5° to 20° C. after the completion of the oxidation reaction, is carried out between after the completion of the salt formation reaction and before the oxidation reaction to obtain 10.3 g (yield based on MPCA: 89.2%) of ammonium salt of N,N-dimethylnicotinamide-2-sulfinic acid.

Referential Example 4

The reaction product obtained according to the oxidation reaction in -Example 13 is used as it is, and procedures of Referential Example 2 are repeated to obtain 6.82 g (yield based on MPCA: 59.6%; purity: 93.8%) of 2-aminosulfonyl-N,N-dimethylnicotinamide.

13. Example 13

Preparation of ACPS salt of the present invention (a) Salt Formation Reaction

A 300 ml four-necked flask equipped with thermometer, dropping funnel and stirrer is charged With 5.0 g (0.0275 mole) of 2-mercapto-N,N-dimethylnicotinamide, 1.2 g (0.03 mole) of sodium hydroxide and 15 ml of water, followed by dissolving with agitation and by reacting at room temperature for 10 minutes to obtain a reaction product containing sodium-N,N-dimethylnicotinamide-2-thiolate.

Separately, a reaction product obtained by carrying out the same reaction as above is thickened, and the deposited crystals are filtered off and dried to isolate 5.53 g of sodium-N,N-dimethylnicotinamide-2-thiolate having a melting point of 260° to 268° C. (a little decomposed).

(b) Oxidation Reaction

Into the reaction product obtained according to the above salt formation reaction, as it is, is dropped with agitation for about 30 minutes 6.23 g (0.055 mole) of 30% aqueous hydrogen peroxide solution at a temperature of 10° to 20° C. externally cooling for reacting to obtain a reaction product containing sodium N,N-dimethylnicotinamide-2-sulfinate.

Separately, a reaction product obtained by carrying out the salt formation reaction and oxidation reaction in the same manner as above is thickened and dried to isolate 6.05 g (yield based on MPCA: 93.2%) of sodium N,N-dimethylnicotinamide-2-sulfinate having a melting point of 260° to 265° C. (colored brown, decomposed).

Referential Example 5

Preparation of APCA: (Amination Reaction)

To the reaction product obtained according to the oxidation reaction in Example 14 as it is, is added 2.48 g (0.03 mole) of sodium acetate at a temperature of 10° to 30° C., and 4.03 g (0.0357 mole) of hydroxylamine-o-sulfonic acid is then added for reacting with agitation for about 5 hours. Crystals deposited at about 20° C. is filtered, washed with water and dried to obtain 4.56 g (yield based on MPCA: 72.4%: purity: 95.3%) of 2-aminosulfonyl-N,N-dimethylnicotinamide.

Referential Example 6

Procedures of Referential Example 14 are repeated except that 1.83 g (0.03 mole) of 28% ammonia water in place of 2.48 g of sodium acetate is used and that the reaction time is 3 hours in place of 5 hours to obtain 4.66 g (yield based on MPCA: 74.0%: purity: 98.2%) of 2-aminosulfonyl-N,N-dimethylnicotinamide.

Referential Example 7

Procedures of Referential Example 5 are repeated except that 4.16 g (0.0412 mole) of triethylamine in place of 2.48 g of sodium acetate is used and that the reaction time is 3 hours in place of 5 hours to obtain 4.35 g (yield based on MPCA: 69.1%: purity: 97.1%) of 2-aminosulfonyl-N,N-dimethylnicotinamide.

14. Example 14

Procedures of Example 14 are repeated except that 15 ml of water used in the salt formation reaction of Example 5 is replaced by 7.5 ml thereof to obtain 6.08 g (yield based on MPCA: 93.7%) of sodium N,N-dimethylnicotinamide-w-sulfinate.

Referential Example 8

Procedures of Referential Example 5 are repeated except that the reaction product obtained according to the oxidation reaction of Example 15 is used as it is, that a step of adding 2.48 g of sodium acetate followed by adding 4.03 g of hydroxylamine-o-sulfonic acid is replaced by a step of adding 4.03 g (0.0357 mole) of hydroxylamine-o-sulfonic acid followed by adding 1.83 g (0.03 mole) of 28% ammonia water, and that the reaction time is 3 hours in place of 5 hours to obtain 4.77 g (yield based on MPCA: 75.8%: purity: 98.3%) of 2-aminosulfonyl-N,N-dimethylnicotinamide.

15. Example 15

Procedures of Example 14 are repeated except that 1.8 g (0.03 mole) of 28% ammonia water in place of 1.2 g of sodium hydroxide is used to obtain 5.90 g (yield based on MPCA: 92.9%) of ammonium salt of N,N-dimethylnicotinamide-2-sulfinic acid.

Referential Example 9

Procedures of Referential Example 5 are repeated except that the reaction product obtained according to the oxidation reaction of Example 16 is used as it is, and that the reaction time is 6 hours in place of 5 hours to obtain 4.68 g (yield based on MPCA: 74.3%: purity: 98.0%) of 2-aminosulfonyl-N,N-dimethylnicotinamide.

16. Example 16

Preparation of ACPS salt of the present invention (a) Polysulfidation Reaction

A mixture of 55.4 g of 2-chloro-N,N-dimethylnicotinamide 24 g of 70% purity sodium hydrosulfide, 96. g of sulfur, 12 g of sodium hydroxide and 15 ml of water is refluxed by heating with agitation for about 2 hours to obtain a reaction product containing 68.7 g of sodium salt of N,N-dimethylnicotinamide-2-(poly)sulfide.

(b) Oxidation Reaction

To the reaction product obtained according to the above polysulfidation reaction in Example 8 are added 180 ml of water and 18 g of a 40% aqueous sodium hydroxide solution, followed by dropping thereinto with agitation for 30 minutes 75.8 g (0.78 mole) of 35% aqueous hydrogen peroxide solution at a temperature of 10° to 20° C. for reacting to obtain a reaction product containing sodium N,N-dimethylnicotinamide-2-sulfinate.

The reaction product thus obtained is subjected to filtration to filter off free sulfur, and the sulfur is washed with water to obtain filtrate and washing liquor.

Separately, polysulfidation reaction and oxidation reaction are carried out in the same manner as above to obtain a reaction product. Similarly, free sulfur is removed from the reaction product, followed by thickening and drying to isolate 65.0 g (yield based on ACHP: 91.8%) of sodium N,N-dimethylnicotinamide-2-sulfinate having a melting point of 258° to 265° C. (colored brown, decomposed).

Referential Example 10

Preparation of APCA: (Amination Reaction)

To a combined solution of the filtrate and the washing liquor obtained according to the oxidation reaction in Example 8 is added 54.24 g (0.48 mole) of hydroxylamine-o-sulfonic acid with agitation at 10° C. or lower to be dissolved, and 48 g (0.48 mole) of 40% aqueous sodium hydroxide solution is then dropped thereinto to be reacted with agitation for 3 hours at a temperature of 10° to 20° C.

A reaction product thus obtained is filtered to obtain crystals, which are washed with water and dried to obtain 52.5 g (yield based on ACHP: 76.4%; purity: 96.5%) of 2-aminosulfonyl-N,N-dimethylnicotinamide.

What is claimed is:

1. A mercapto-substituted pyridine compound having formula (I'):

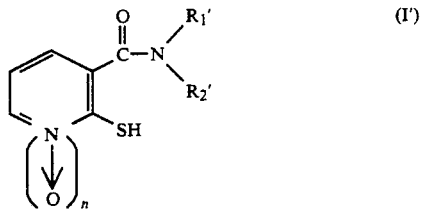

where $R_1$ and $R_2$ are $C_{1-6}$ alkyl groups, n is 0 or 1, or a salt thereof.

2. A compound or salt thereof as claimed in claim 1, wherein n in formula (I') is 0.

3. A compound or salt thereof as claimed in claim 1, wherein, in formula (I'), $R_1$ is a methyl group and $R_2$ is a methyl group.

4. A compound or salt thereof as claimed in claim 1, wherein said mercapto-substituted pyridine compound is N,N-dimethyl-2-mercapto-nicotinamide.

* * * * *

UNITED STATES PATENT AND TRADEMARK OFFICE
CERTIFICATE OF CORRECTION

PATENT NO. : 5,168,113

DATED : December 1, 1992

INVENTOR(S) : Takahiro Haga, Tatsuo Isogai, Shigeo Murai, Hisayoshi Jonishi, Tokiya Kimura, Hiroshi Sasaki, Takao Awazu, Toshihiro Tanaka and Yasuhiro Tsujii It is certified that error appears in the above-identified patent and that said Letters Patent is hereby corrected as shown below:

On the title page, --[73] Assignee: Ishihara Sangyo Kaisha Ltd., Osaka, Japan--.

Signed and Sealed this

Twenty-eighth Day of December, 1993

Attest:

BRUCE LEHMAN

Attesting Officer

Commissioner of Patents and Trademarks